(12) United States Patent
Duncan

(10) Patent No.: US 11,131,569 B2
(45) Date of Patent: Sep. 28, 2021

(54) HAND HELD MOISTURE METER IN-FIELD CALIBRATION

(71) Applicant: Wagner Electronic Products, Inc., Rogue River, OR (US)

(72) Inventor: Timothy Duncan, Grants Pass, OR (US)

(73) Assignee: Wagner Electronic Products, Inc., Rogue River, OR (US)

(*) Notice: Subject to any disclaimer, the term of this patent is extended or adjusted under 35 U.S.C. 154(b) by 143 days.

(21) Appl. No.: 16/653,406

(22) Filed: Oct. 15, 2019

(65) Prior Publication Data

US 2020/0132524 A1   Apr. 30, 2020

Related U.S. Application Data

(60) Provisional application No. 62/753,674, filed on Oct. 31, 2018.

(51) Int. Cl.
*G01D 18/00* (2006.01)
*G01N 27/22* (2006.01)

(52) U.S. Cl.
CPC ......... *G01D 18/006* (2013.01); *G01N 27/223* (2013.01)

(58) Field of Classification Search
CPC .... G01D 18/006; G01N 27/223; G01N 33/46; G01F 1/6842; G01F 1/684; G01F 5/00; G01F 1/68; G01F 1/6845; G01F 1/3218; G01F 1/32

USPC ................ 73/861.22, 202.5, 204.11
See application file for complete search history.

(56) References Cited

U.S. PATENT DOCUMENTS

| | | | | |
|---|---|---|---|---|
| 5,817,231 A | * | 10/1998 | Souza | B01D 61/08 |
| | | | | 210/96.2 |
| 2008/0316051 A1 | * | 12/2008 | Salser, Jr. | H04Q 9/00 |
| | | | | 340/870.02 |
| 2013/0186440 A1 | * | 7/2013 | Boyer | A47L 15/0023 |
| | | | | 134/56 D |
| 2016/0278651 A1 | * | 9/2016 | Lu | A61B 5/085 |

\* cited by examiner

*Primary Examiner* — Christopher P McAndrew
*Assistant Examiner* — Zannatul Ferdous
(74) *Attorney, Agent, or Firm* — Klarquist Sparkman, LLP

(57) ABSTRACT

Methods and apparatus are disclosed for calibration determinations for handheld moisture meters in the field. A calibration reference stand emulates a sample with an equivalent moisture content, allowing rapid determination whether a moisture meter is out of calibration, or determination of a new calibration value. The calibration reference stand includes an electromagnetic load, which can be formed of a metal sheet or high dielectric constant material, supported on a platform, and mechanical fixturing for reproducible positioning of a moisture meter on the stand. Associated methods and variations are disclosed.

11 Claims, 8 Drawing Sheets

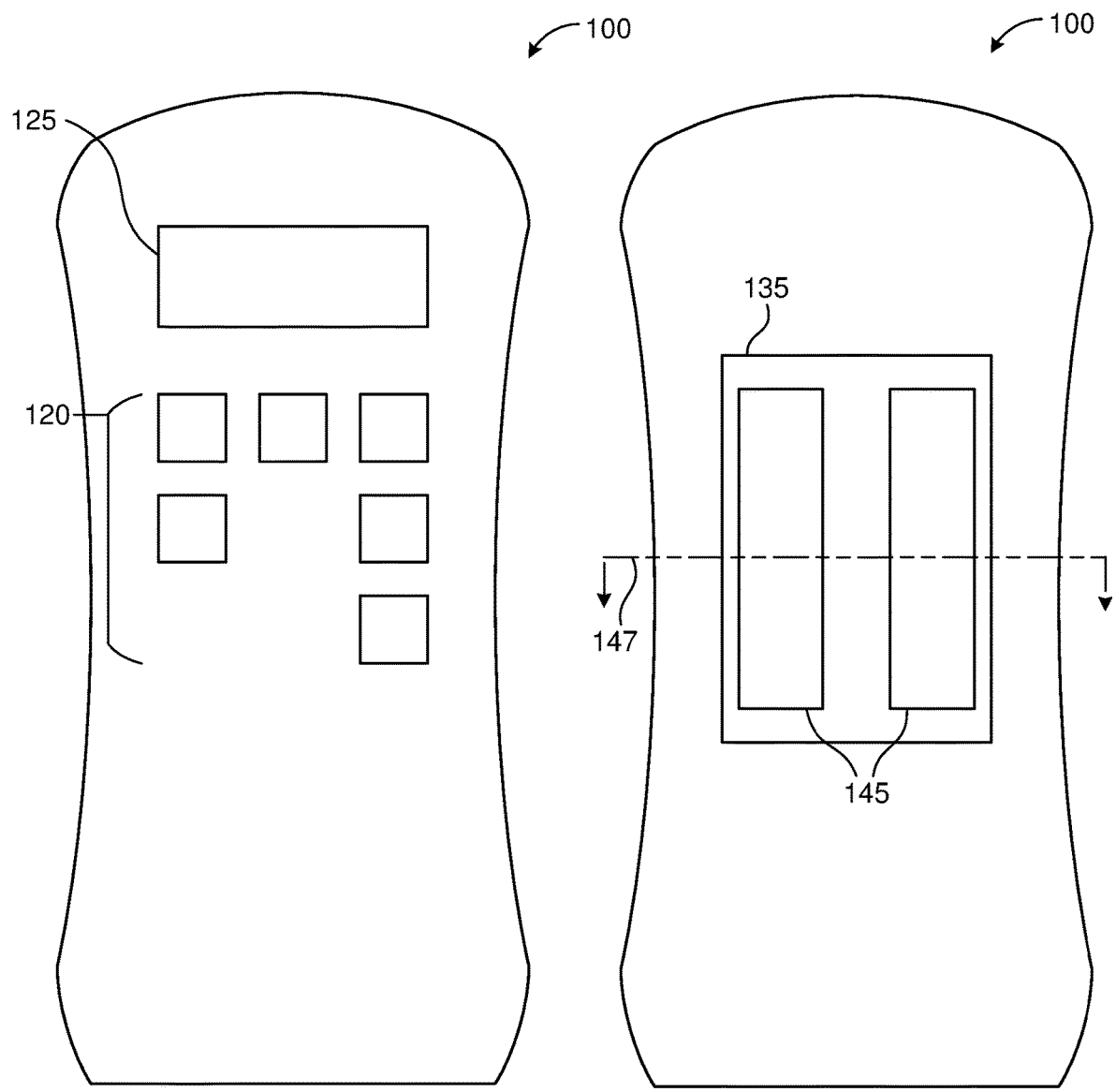
FIG. 1A   FIG. 1B

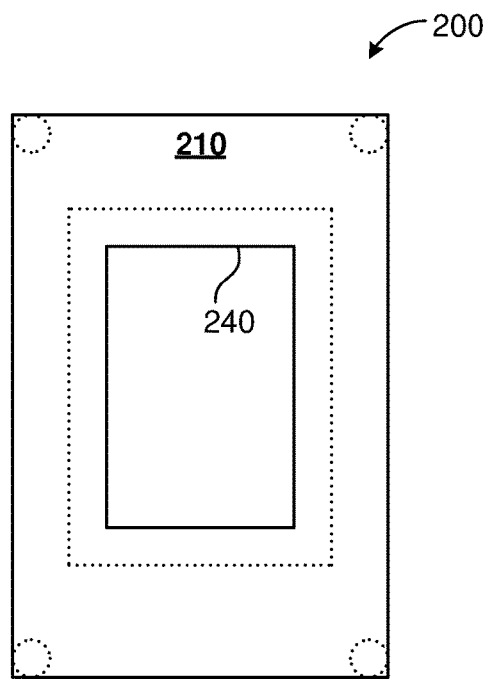
FIG. 2A
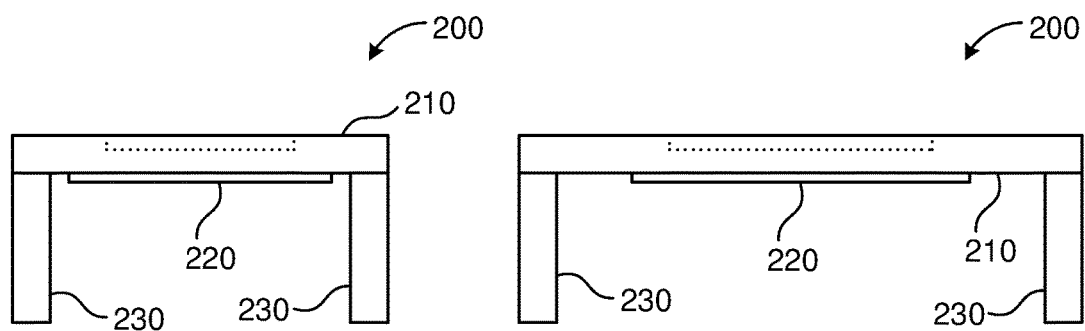
FIG. 2B  FIG. 2C

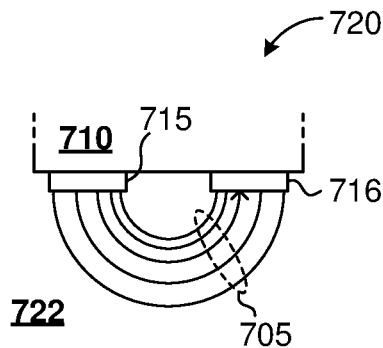
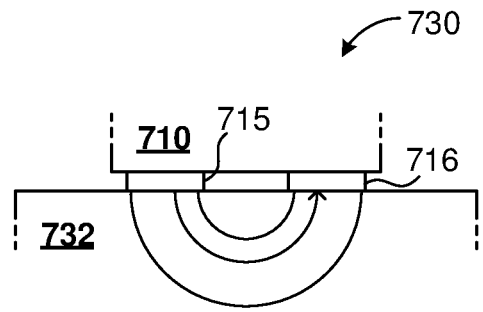
FIG. 7A  FIG. 7B
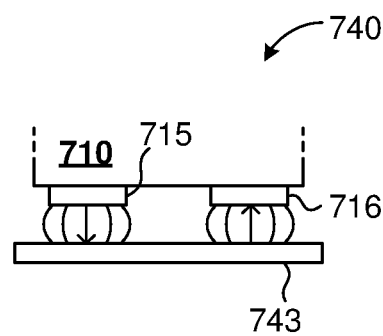
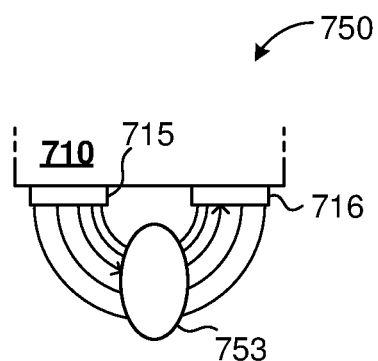
FIG. 7C  FIG. 7D
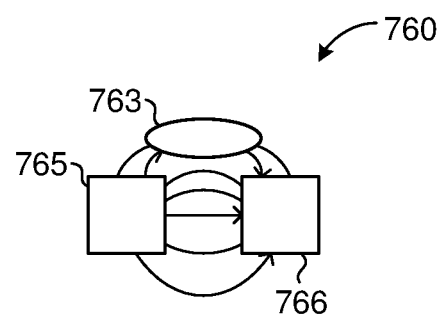
FIG. 7E

HAND HELD MOISTURE METER IN-FIELD CALIBRATION

CROSS REFERENCE TO RELATED APPLICATION

This application claims the benefit of U.S. Provisional Application No. 62/753,674, entitled "HAND HELD MOISTURE METER IN-FIELD CALIBRATION," filed Oct. 31, 2018, which application is incorporated by reference herein in its entirety.

FIELD

This application describes the invention of a device that enables an in-field calibration determination for a handheld moisture meter.

BACKGROUND

Moisture measurements can be important for quality control at various stages of manufacture of wood products, and also subsequently during their operational life. Moisture measurements are also important is assessing condition of other materials such as concrete, drywall, paint, sand, or soil. Handheld moisture meters can be convenient for making such measurements, but can drift out of calibration over time, resulting in inaccurate measurements. Sending a meter back to the factory for recalibration can be tedious and time-consuming, particularly when recalibration is not required. Accordingly, there remains a need for improved technology that can be used in the field to check whether a moisture meter is out of calibration, or to recalibrate the moisture meter.

SUMMARY

In summary, the detailed description is directed to various innovative technologies associated with in-field calibration of a moisture meter. Some examples of the disclosed technology use a test measurement with the moisture meter placed atop a portable calibration reference stand to determine whether the moisture meter is out of calibration, or to recalibrate the moisture meter.

In certain examples, the disclosed technologies can be implemented as a computer-implemented method. An input to trigger a calibration determination is received at the moisture meter, and a measurement of a calibration reference stand is obtained with the moisture meter. The measurement is analyzed, with reference to a predetermined calibration reference stand, and based on the moisture meter being positioned on a sensor pad of the calibration reference stand. The calibration determination is made based on the analysis of the measurement.

In some examples, the calibration determination can be that the moisture meter is out of calibration, while in other examples, the calibration determination can be a first new calibration value of the moisture meter. The new calibration value can be stored in non-volatile memory of the moisture meter. Further, a user can be prompted to position the moisture meter in a second position, which can be spatially apart from any electromagnetic load. Responsive to the meter being positioned in the second position, a second measurement can be obtained with the moisture meter, and a second new calibration value can be determined for the moisture meter. Based on the first and second new calibration values, multiple updated calibration values, covering a measurement range of the moisture meter, can be determined and stored in non-volatile memory of the moisture meter.

In certain examples, the disclosed technologies can be implemented as a calibration reference stand incorporating a platform, a sensor pad, and an electromagnetic load. The sensor pad defines a location at which a sensor of a moisture meter can be placed, and the electromagnetic load is positioned spatially apart from that location. The calibration reference stand is configured a load to the sensor that is equivalent to a predetermined moisture content value, when the sensor is positioned at the location defined by the sensor pad.

In some examples, the location for placing the sensor on the sensor pad can be defined by one or more structural features, such as a rectangular relief at a surface of the sensor pad. The structural feature(s) can facilitate reproducible positioning of the sensor at the location. In further examples, the electromagnetic load can be a metal sheet, and can extend spatially beyond the sensor in at least one direction, when the sensor is positioned at the location defined by the sensor pad. The platform can include an insulator, at least part of which can be positioned between the electromagnetic load and the location defined by the sensor pad. The calibration reference stand can include legs extending down from the platform. The calibration reference stand and the moisture meter can be individually matched to each other.

In additional examples, the disclosed technologies can be implemented as a system incorporating the calibration reference stand and the moisture meter. The moisture meter can include a sensor, one or more processors, writable non-volatile storage for new or predetermined calibration values, and one or more computer-readable media storing instructions for performing any of the disclosed methods.

In certain examples, the disclosed technologies can be implemented as a method. A moisture meter is calibrated with a traceable standard. A calibration reference stand is provided, and a reference value is determined for a combination of the moisture meter and the calibration reference stand. The reference value is stored in non-volatile memory.

In some examples, the non-volatile memory can be within the moisture meter, while in other examples, the non-volatile memory can be external to the moisture meter and accessible from the moisture meter over a network. In additional examples, the method can include determining a test value for the combination of the moisture meter and the calibration reference stand, comparing the test value and the reference value and, based on the comparing, making a determination regarding calibration of the moisture meter.

The innovations can be implemented as part of one or more methods, as part of one or more instruments or computing systems adapted to perform an innovative method, or as part of non-transitory computer-readable media storing computer-executable instructions for causing an instrument or computing system to perform the innovative methods. The foregoing and other objects, features, and advantages of the invention will become more apparent from the following detailed description, which proceeds with reference to the accompanying figures.

BRIEF DESCRIPTION OF THE DRAWINGS

FIGS. 1A-1B depict top and bottom views of an example handheld moisture meter suitable for implementing disclosed technologies.

FIGS. 2A-2C depict plan, elevation, and profile views of an example calibration reference stand according to the disclosed technologies.

FIGS. 7A-7E are diagrams illustrating field patterns for several example configurations of a moisture meter with or without a coupled electromagnetic load according to the disclosed technologies.

DETAILED DESCRIPTION

Introduction

Figure 3:
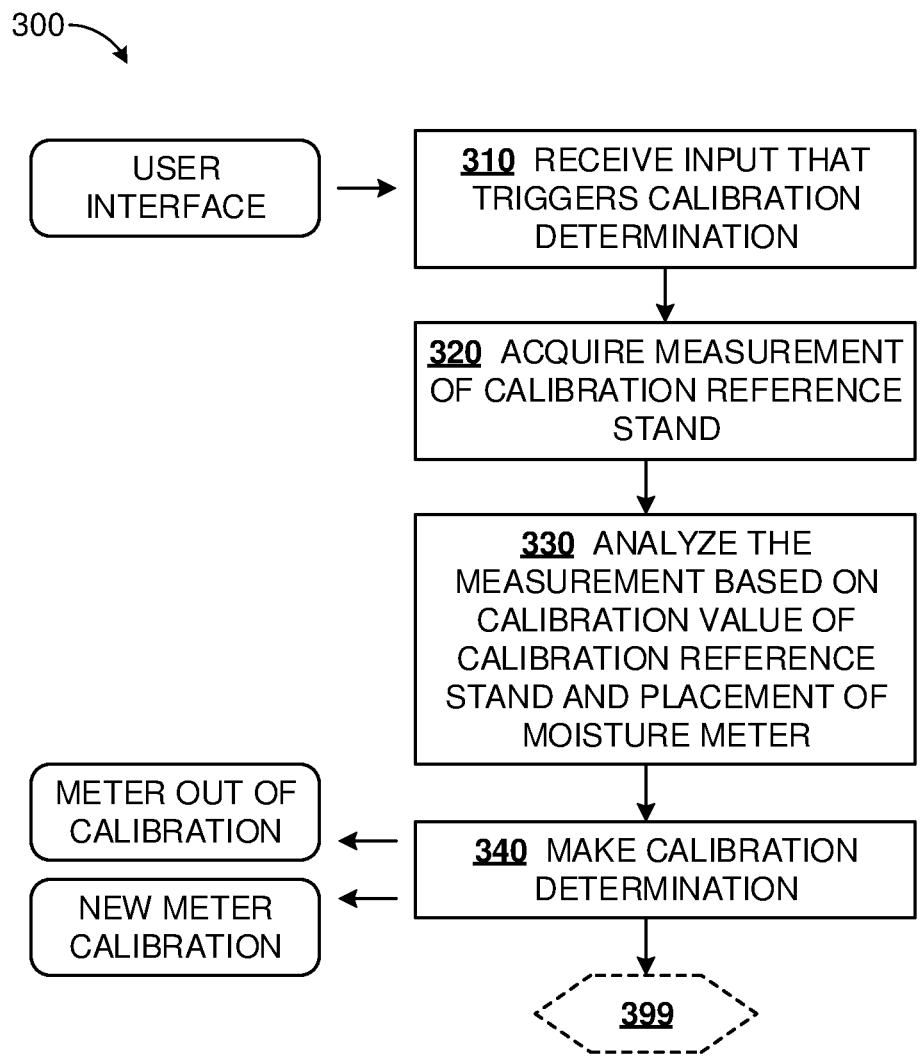
FIG. 3 is a flowchart of a first example method according to the disclosed technologies.

Capacitive based wood moisture measurement can be performed by the measurement of a wood sample placed within the electric field region of a capacitor having two electrode plates. The moisture within the sample can act as a dielectric material within the capacitor. The dielectric constant or permittivity of the wood sample can be proportional to the moisture content of the wood sample, and can affect the capacitance of the capacitor accordingly. The meter can measure the capacitance of the moisture-containing wood sample, from which the moisture content can be determined. This type of meter can be calibrated to provide a direct indication of the moisture content of the wood sample. The meter can be calibrated by measuring one or more samples of known moisture content. Based on measurements of two samples of different known moisture content, and using a linear calibration model, the meter can be calibrated at the two known moisture content values, and the calibration can be extended to cover the measurement range of the moisture meter by extrapolation or interpolation, so as to provide calibrated moisture content measurements of unknown samples.

In some examples, air can be used for one of the known moisture content values. Because moisture content values are measured as percent by weight of, commonly, a solid sample, the moisture content of even high humidity air can be insignificant relative to the scales of moisture content in sample materials. (At 25° C., the saturated water vapor density of air, i.e. 100% relative humidity, is about 20 μg/cm$^3$, equivalent to less than 0.003% moisture content of common wood materials.)

At the factory, a calibration standard can be used as the other known sample. For example, a calibration standard can be known to have 16.1% moisture content, or to be equivalent to 16.1% moisture content, in a particular wood material. Calibrations can vary according to the specific material, e.g. oak and pine can have different calibrations, due to factors including variations is wood density, and the presence of both bound water (within plant cells constituting the wood material) and free water (external to the plant cells) within the material.

In some examples, the calibration standard can be a sealed device containing moisture, while in other examples, the calibration standard can be an equivalent electromagnetic load that emulates a moisture-containing sample by increasing the capacitance measured by a moisture meter. It can be desirable for the calibration standard to be impervious to external moisture and to have long term stability. Metal can be used as an electromagnetic load in a calibration standard.

In some examples, the calibration standard can itself be calibrated by a procedure dubbed a "dry-down" experiment. The calibration standard and a number of samples having varying moisture content can be measured with a reference moisture meter. Each sample can be weighed in its measured moist state, dried to 0% moisture content ("oven-dry") in an oven, and weighed in its dry state, to ascertain the moisture content in the moist state. Then, by plotting a graph of reference meter readings against moisture content of the several samples, the measurement of the calibration standard can be located on this graph, and an accurate equivalent moisture content for the calibration standard can be read off the graph. Because the plotted sample moisture contents can be determined from fundamental measurements of weight, the calibration standard calibrated by the dry-down experiment can be regarded as an authoritative standard. If the weights are determined by a scale having NIST traceable calibration, then a dry-down procedure can result in a NIST-traceable calibration standard. In other examples, the calibration standard can be calibrated and certified against a NIST traceable moisture or moisture meter standard, which can also result in an authoritative (NIST traceable) calibration standard.

However, moisture meters contain electronic components whose values can drift over time, causing the meter to lose accuracy. A conventional approach can require sending the meter back to the factory for periodic recalibration, however this can be impractical and can result in downtime for the meter. As an alternative, authoritative calibration standards could be provided to users, however the dry-down experiment can be tedious to replicate at the scale on which moisture meters can be manufactured, and this can also be impractical.

The present technology provides a calibration reference stand, which can be produced with simpler methods than required for a calibration standard, and can be manufactured at scale and distributed widely to users. It can be practical to have temporally stable calibration reference stands matched to respective moisture meters at the time of manufacture. Individual calibration reference stands matched to each moisture meter can also provide greater accuracy than having generic calibration reference stands that are supposed to be identical but in practice can have variations. A calibration reference stand may not be an authoritative calibration standard, but can provide a practical way for users of moisture meters to maintain their instruments in serviceable condition.

Example Moisture Meter

FIG. 1A depicts a top view of an example handheld moisture meter 100 suitable for use with disclosed technologies. Meter 100 can have a size and weight suitable to be held in a user's hand. The top surface can accommodate a keypad 120 comprising a plurality of keys which can be touch-sensitive keys, proximity-sensitive keys, or pushbuttons. The top surface can also include a display 125, which can be a segmented display, a pixelated screen, or can include one or more annunciators for specific functions. The functions of display 125 and keypad 120 can be integrated, for example as a touchscreen keypad, or as one or more softkeys in which a current function of a key of keypad 120 is indicated on the display 125.

FIG. 1B depicts a bottom view of the moisture meter 100. A moisture sensor comprising two electrodes 145 can be placed on or near a bottom surface of the meter 100. One or more moisture readings can be taken with the bottom surface of the moisture meter placed in contact with a sample whose moisture is to be measured. In some examples, electrodes 145 can be printed or photolithographically etched metallic regions on a surface of a printed wiring board 135, and can be covered by a layer of solder mask or another insulator (not shown) to protect the electrodes. FIG. 1B also shows a section line 147 described further herein.

Numerous variations are possible within the scope of this disclosure. While rectangular electrodes 145 of equal size are shown for simplicity of illustration, this is not a requirement. Unequal electrode sizes or other electrode shapes can also be used, such as round, annular, spiral, or arrays of electrodes in an interleaved or interlocking pattern. The plane of electrodes 145 can be flush, recessed, or protruding with respect to a bottom surface of a housing of the meter 100. Meter 100 can incorporate multiple sets of electrodes 145 for different operating modes such as for different penetration depths or different materials. The multiple sets of electrodes can be independent or can share a common electrode.

Terminology

The usage and meaning of all quoted terms in this section apply throughout this disclosure unless clearly indicated otherwise or repugnant to the context. The terminology below extends to related word forms.

An "alert" is an indication of an abnormal condition, such as a reading that is outside an acceptance band or outside a valid range. Alerts can be provided audibly, visually, haptically, or by a transmitted message, in any combination. An audible alert can be a beep, a tone sequence, a programmable sound, a synthesized or playback voice message. A visual alert can be a lamp, display message, or other display annunciator, and can be pulsed, steady, or flashing. A haptic alert can be a vibration of the moisture meter or associated device. Generally, an alert can be presented directly by the moisture meter, or by an associated computing device such as a smartphone, a wearable appliance, or another portable or stationary computing device. Messages can be sent over a network, e.g. to be logged at a material requirements planning (MRP) enterprise data system.

The term "calibration" refers to a procedure for configuring an instrument to improve accuracy of output (e.g. readings) provided by the instrument. The term calibration can also be used to qualify values, data, devices, or other objects associated with a calibration procedure. A "calibration value" is a numerical quantity that can be used (e.g. as a coefficient, offset, or index) to convert an uncalibrated measurement into a calibrated reading. An instrument can be said to be "out of calibration" if its output is not accurate to within a predetermined tolerance.

A "calibration reference stand" is a device configured to receive a moisture meter in a defined position and present a known electromagnetic load to the moisture meter. With the moisture meter in place on the calibration reference stand, particular measurements can be made for the purpose of determining a calibration state of the moisture meter, or for recalibrating the moisture meter.

A "comparison" between two quantities Q1, Q2 is any operation involving a greater than operator (e.g. Q1>Q2), a less than operator (e.g. Q1<Q2), subtraction (e.g. Q1−Q2, |Q2−Q1|), or division (e.g. Q1/Q2, Q2/Q1) applied to the quantities Q1 and Q2. Comparison can include checking whether the result of such operation is within a tolerance range, or above or below a threshold. Comparison can include scaling one or both quantities Q1, Q2 to a like unit before performing the comparison operation.

An "electromagnetic load" is an object that can perturb the sensed volume of a capacitance detecting meter to change the measured capacitance. Some electromagnetic loads can increase the detected capacitance by a factor of at least 7, 10, 20, 50, 80 or even more, as compared to having air filling the sensed volume. Electromagnetic loads can be formed of metal, water, or another high-k material (e.g. a material having dielectric constant k>7), in any combination. An electromagnetic load formed of water or a high-k dielectric can also be dubbed a "dielectric load".

The term "handheld" refers to any device that has a size and weight suitable for being held in a person's hand. Characteristic dimensions of a handheld device can be in the range 1 cm-1 meter and often between 2 cm-20 cm inclusive. Characteristic weights of a handheld device can be in the range 1 g-5 kg and often between 50 g-500 g. The term handheld characterizes a class of device, and does not require that the device actually be held in a person's hand for the disclosed technologies to be used. For example, a handheld moisture meter could be operated by a robotic arm, or mounted on a frame while the sample to be measured is moved along the meter.

An "insulator" is a material whose internal electric charges do not flow freely. Insulators can be approximated as having zero current flow through them or infinite resistance, with voltage applied. Common polymers can be insulators, as can wood, concrete, paper, and a host of other common materials. In this disclosure, a distinction is sometimes made between insulators that are impervious to moisture, and those that can exchange moisture with their environment. The former can be suitable for use in a calibration reference stand, while the latter can be suitable candidates for moisture measurement with a moisture meter.

The term "match" refers to a property of two objects or devices that have a known operating characteristic when the two are used together. In this disclosure, a calibration reference stand can be matched to a moisture meter.

A "measurement" refers to a digitized value indicative of a physical quantity detected by a sensor, optionally including some preprocessing (such as averaging, scaling, or transformation according to underlying physics of a sensor and its circuitry). A measurement m can generally be uncalibrated, but can be converted to a calibrated reading M through the application of a calibration formula M=Cal(m). In this disclosure, some measurements can be capacitance detected by the moisture meter between its sensor electrodes. Measurements can be described as counts (e.g. counts of analog-to-digital converter units, or an integer in a digital register) but this is not a requirement.

A "measurement range" is an interval of values of a physical quantity over which the quantity can be measured. For example, a moisture meter can have a measurement range of e.g. 0-32% MC in a particular wood.

"Moisture" or "moisture content" refer to water contained within another material, or the amount thereof. Commonly, moisture content can be reported as percent by weight of the sample, denoted "% MC". However this is not a requirement, and moisture content can also be reported as an absolute density of the water present. Commonly, the percent by weight can be referred to the dry weight of the sample. To illustrate, a sample having dry weight 100 g, which has absorbed 25 g water to reach a total moist weight of 125 g, can be reported as 25/100=25% MC. However, in other applications, the percentage moisture content can be referred to the total weight of the moist sample. Thus, referred to the moist weight, the illustration above could be reported as 25/125=20% MC. Moisture content can vary both spatially over the sample, and over time.

A "moisture meter" is an instrument for measuring moisture content of a sample.

A "moisture sensor" is a device that can be used to generate a signal dependent on moisture present in the vicinity of the moisture sensor. A moisture sensor can be integrated into a moisture meter. Some example moisture sensors described herein are intended for electrical measurements, however this is not a requirement. The disclosed technologies can be employed with e.g. optical or other types of moisture sensors as well. An electrical moisture sensor can be a combination of two or more electrodes (sometimes, "sensor electrodes") that can be coupled with electronics to make a measurement indicative of moisture. Example moisture sensors can operate on resistive or capacitive principles. A capacitive moisture sensor can be used to generate electric fields between the electrodes and penetrating into a sample, so that coupled electronics can measure e.g. (a) charging current on an electrode with voltage applied across a pair of the electrodes, (b) voltage with charging current applied, or (c) oscillating frequency of a tank circuit incorporating the capacitance between two electrodes. In one of these ways, or a variation thereof, the capacitance of the sample between the sensor electrodes can be determined, which can indicate the moisture content within the sample. A resistive moisture sensor can be used to pass current from one electrode to another, allowing coupled electronics to measure the current or resistance between the electrodes with a voltage applied across the electrodes, or to measure voltage across the electrodes with current driven between the electrodes, in order to determine the resistance between the electrodes (through the sample), which can indicate the moisture content within the sample. The coupled electronics can serve to apply a stimulus signal to the sensor electrodes, to filter or amplify a response signal in a circuit incorporating the sensor electrodes, or to digitize the response signal after any filtering or amplification, in any combination. Portions of the associated electronics, such as an analog-to-digital converter (ADC), can be incorporated in a same integrated circuit (IC) as a microprocessor.

A "notification" is an indication of an event, which can be a normal event, such as a meter entering a particular mode or acquiring a measurement. Similar to an alert, a notification can be provided audibly, visually, haptically, or by a transmitted message, in any combination. Notifications can be provided at or by a moisture meter, at an associated device, or logged remotely.

A "reading" refers to a value of a measured quantity, particularly moisture content, suitable for presentation to a user or for incorporation into statistics. Typically, a reading can be obtained from a measurement by scaling or calibration, and can be presented in predefined units. For example, a moisture reading could be 11% MC calibrated for pine, or 0.08 g/cm$^3$ as an absolute water density.

The term "sample" refers to any object or material on which moisture measurements are being made.

A "sensor pad" is a structural feature of a calibration reference stand on which a moisture sensor of a moisture meter can be placed in a defined position.

A "test value" is a value of a measurement, reading, or related quantity obtained from a test performed in the field. A "reference value" is a corresponding value of a measurement, reading, or related quantity obtained at the factory or at the time of manufacture. In this disclosure, one or more test values can be compared with corresponding reference values to determine a state (e.g. out of calibration) of a moisture meter, or to determine one or more new calibration values for the moisture meter.

A "traceable standard" is a device having a known reference value of a physical parameter, with a specified accuracy relative to an authoritative standard for that physical parameter. Traceability can be evidenced by an unbroken chain of comparisons leading back to the authoritative standard. An "authoritative standard" can be a standard maintained by NIST or another government agency, or a standard whose reference value is derived from fundamental measurements.

The terms "top," "bottom," "down" and the like are used for convenience. For example, in a common configuration, the bottom of a handheld meter can be placed on a top surface of a sample. However, one of ordinary skill will understand from this disclosure that a choice of actual orientation can be varied without departing from the scope of the disclosed technologies.

The term "trigger" refers to causation of an operation or sequence of operations, or to a proximate cause of such operation or sequence of operations.

Example Calibration Reference Stand

FIGS. 2A-2C depict plan, elevation, and profile views of an example calibration reference stand 200 according to the disclosed technologies. As seen in top view FIG. 2A, the stand 200 includes a sensor pad 240 supported on a platform 210. The sensor pad 240 defines a location at which a sensor of a moisture meter can be received. For example, the sensor 145 of moisture meter 100 of FIG. 1 can have a support board 135 which fits the sensor pad 240. Support board 135 can protrude from the bottom of moisture meter 100, and sensor pad 240 can be recessed relative to the platform 210, or vice versa, so that the sensor of moisture meter can be received with reproducible positioning at the sensor pad.

As can be seen in dotted lines of FIGS. 2B-2C, the illustrated sensor pad 240 can be formed as a rectangular relief (i.e. a recess) in the top surface of platform 210, however this is not a requirement. Other structural features of the sensor pad 240 can also be used to define a location at which the sensor of moisture meter 100 can be reproducibly positioned. Furthermore, the top surface of platform 210 can include other structural features to accommodate structural features of the bottom of the moisture meter, or for purposes of design.

FIGS. 2B-2C also show an electromagnetic load 220 supported on an underside of the platform 210. The load 220 is shown as a sheet, which can be a metal sheet or a material of high dielectric constant, however this is not a requirement. Other shapes and positioning of the load 220 can be employed, as described herein. When the sensor 145 of meter 100 is suitably positioned at the location defined by sensor pad 240, the load 220 can present a load to the moisture sensor 145 of meter 100 that emulates a sample with some equivalent moisture content. As illustrated in FIGS. 2B-2C, the load 220 extends beyond the extent of sensor pad 240 in both transverse directions. Thereby, the load can also extend beyond a sensor positioned within the recess of sensor pad 240. In some examples, a metal sheet used as load 220 can also serve as a printed or stamped label of the calibration reference stand, with a serial number, calibration value, instructions or other information presented thereon.

In some examples, the platform 210 can be made of a moisture-free insulating material, such as a polymer, including thermoplastics or thermosetting polymers, commonly dubbed "plastic". The platform material can act as a spacer between the electromagnetic load 220 and a moisture sensor placed on the sensor pad 240. The platform material can be physically located between the electromagnetic load 220 and the moisture sensor placed on sensor pad 240. A low dielectric insulating material (e.g. having dielectric constant k<7) can minimize or prevent undue effects on the coupling of the electromagnetic load and the moisture sensor. In examples, the transverse size of a calibration reference stand 200 can be proportionate to the size of a handheld moisture meter, or large enough to stably support the moisture meter. Thus, the length can be in a range 5-30 cm, often 10-17 cm, or about 13.7 cm. The width can be in a range 5-20 cm, often 8-15 cm, or about 11.7 cm.

Platform 210 can be supported on legs 230, so as to avoid interfering effects of moisture in a table or other support structure on which stand 200 is placed. The height of the stand 200 can be proportionate to the intended measurement depths within samples. In examples, the height can be in a range 0.5-10 cm, often 1.5-6 cm, or about 3.2 cm.

Example Uses of a Calibration Reference Stand

This section describes some illustrative and non-limiting uses of a calibration reference stand.

Use at Manufacturing Time

At manufacturing time, a moisture meter can be calibrated with reference to an authoritative calibration standard. Thereby, the moisture meter can provide calibrated moisture content readings of a specified accuracy (e.g. 1% MC) over a measurement range (e.g. 0-32% MC) and for one or more specified materials (e.g. pine, oak) at the time of manufacture. The calibrated moisture meter can be used to obtain a measurement (e.g. in counts) or a reading (e.g. in % MC) with a particular calibration reference stand. Based on this measurement or reading, a reference value R can be derived and stored in the meter for future reference. Additional aspects of this use are described further herein, for example in context of FIG. 5.

In some examples, the reference value R can be a direct ratio or difference of the measurement or reading A of the calibration reference stand and a default value D. So, any of A-D, A/D, D/A, or D-A can be used as the reference value R, suitably scaled or formatted for a digital representation. In some examples, the default value D can be a measurement or reading S obtained with the same meter and the authoritative calibration standard, i.e. D=S. Additionally, R can be encoded together with additional information.

As an illustration, if S=300 (a measurement of 300 counts) and A=292, then a factor Offset O for the combination of moisture meter can be calculated, with scaling, as O=50+Round(1000·(A/S−1)). The term in parentheses represents the fractional deviation of the measurement from ideal, i.e. if the calibration reference stand was an exact replica of the authoritative calibration standard; the term 1000 scales the equivalent moisture value of the authoritative standard to 1000 counts; and the term 50 provides an additive offset so that the result O is an unsigned positive integer between 0 and 99 inclusive, even if A<S. In this illustration, O=50+Round(1000·(292/300−1))=50+Round(−26.67)=50−27=23. Then, a tolerance can be assigned for the meter and calibration reference stand. To illustrate, a tolerance can be TOL=1% MC, and can be coded in units of ¼% MC, as TOL'=4. Finally, the value of R can be obtained with the equation R=100·TOL'+O. In this illustration, R=100·4+23=423.

Given the stored value of R, the values of TOL'=⌊R/100⌋ and O=R−100·TOL' can subsequently be obtained, as also A≅S·(1+(O−50)/1000)=291.9≅292, which was the original measurement. Thus, at a later time, the stored value of A can be compared with a new measurement of A to determine the extent to which the meter has drifted.

The reference value R can take many forms. For example, the measured value A or the offset O can be stored as the reference value, with or without encoding. A moisture meter can store more than one reference value for respective modes of operation. Modes can include sensing depth (e.g. ¼" or ¾"), material (e.g. pine, oak, or concrete), accuracy, or other parameters.

Determining Out-of-Calibration in the Field

In the field, a moisture meter can be tested using the calibration reference stand provided for that meter. To perform the test, the moisture meter can be placed in a calibration mode by a suitable keypad sequence, and placed on the calibration reference stand. A further keypad sequence can trigger a measurement. This value is similar to the A measurement above and can be denoted as B. A comparison of B with A can lead to a determination that the moisture meter is out of calibration. Additional aspects of this use are described further herein, for example in context of FIG. 3 or FIG. 6.

Rather than compare measurements A and B directly, it can be desirable to perform the comparison in units of % MC, because the allowed tolerance TOL is also in units of % MC. The stored calibration formula in the meter can utilize straight line coefficients C0, C1 to convert a measurement m into a moisture content value M according to a formula: M=C1·m+C0. To continue the illustration above, consider C0=−1.9 and C1=0.0600. Then, with the calibration standard, m=S=300, and M=0.0600·300−1.9=18−1.9=16.1 in units of % MC, which can be the equivalent moisture content value of the calibration standard. With the calibration reference stand, the factory measurement m=A=292 yields M=0.0600·292·1.9=15.6% MC. The same formula can be applied to the new measurement B.

If B=312, then M evaluates to 16.8% MC, which is more than 1% away from the factory measurement, i.e. |M(B)−M(A)|>TOL, and the moisture meter can provide an alert indicating that the meter is out of calibration. However, if B=280, then M evaluates to 14.9% MC, which is within tolerance, i.e. |M(B)−M(A)|≤TOL, and no alert can be provided.

Determining New Calibration in the Field

In the field, a moisture meter can be recalibrated using the calibration reference stand provided for that meter. To perform recalibration, the moisture meter can be placed in a recalibration mode by a suitable keypad sequence, and placed on the calibration reference stand. A further keypad sequence can trigger a measurement, following which a user can be prompted to hold the meter in air for 5 seconds, and causing a second air measurement to be taken automatically during the 5 second window. These measurements can be denoted as B1 (on the calibration reference stand) and B0 (in air), and can be used to determine new calibration values for the moisture meter. Additional aspects of this use are described further herein, for example in context of FIGS. 3-4 or FIG. 6. In some examples, the recalibration can be contingent on a finding of out-of-calibration as described herein.

To continue with the illustration above, the factory calibrated instrument read 14.9% MC on the calibration reference stand and 0.0% MC in air. To restore the meter to its factory calibrated condition, new values $C0'$ and $C1'$ can be calculated using $B0$ and $B1$. That is, by the pair of simultaneous equations $C1'\cdot B1+C0'=14.9$ and $C1'\cdot B0+C0'=0.0$ can be solved to obtain $C1'=14.9/(B1-B0)$ and $C0'=-C1'\cdot B0$. To illustrate, if $B1=303$ and $B0=5$, then $C1'=14.9/(B1-B0)=14.9/298=0.0500$, and $C0'=-0.25$. With these new calibration values, $M'=C1'\cdot m+C0'$, and $M'(B0)=0.0500\cdot 5-0.25=0.25-0.25=0.0\%$ MC. Similarly, $M'(B1)=0.0500\cdot 303-0.25=15.15-0.25=14.9\%$ MC, just as obtained at the factory.

First Example Method

FIG. 3 is a flowchart 300 of a first example method according to the disclosed technologies. This method describes making a calibration determination, for a moisture meter, with the aid of a calibration reference stand. The calibration determination can be a determination that the moisture meter is out of calibration, or can be a determination of one or more new calibration values. The method can be performed by a microprocessor or other computing device on board the moisture meter.

At process block 310, the moisture meter can receive an input that triggers the calibration determination. The input can be received from a user interface, e.g. by a keypress, a sequence of entries, or menu navigation. The input can imply that the moisture meter has been placed on a calibration reference stand, as described further herein.

Responsive to this input, at process block 320 the moisture meter can acquire a measurement, to be interpreted as a measurement of the calibration reference stand. In examples, the measurement can be a measurement of capacitance, resistance, or frequency based on an electrical signal passed between the electrodes. At process block 330, the measurement can be analyzed, based on a predetermined calibration value of the calibration reference stand. In examples, the measurement can be converted to a moisture reading in % MC, or the measurement can be transformed into a number of counts comparable with a stored calibration value of the calibration reference stand. The analysis can also be based on the moisture meter having been positioned on a sensor pad of the calibration reference stand, as described further herein.

Then, at process block 340, a calibration determination can be made, based on the analysis. For example, the acquired measurement can be outside an expected range based on the predetermined calibration value of the calibration reference stand, and the moisture meter can be determined to be "out of calibration." Alternatively, the acquired measurement can be within the expected range and the calibration reference stand can be determined to be "in calibration." In further examples, the calibration determination can be a new computed calibration value for the moisture meter. The new calibration value can be determined so that the moisture meter provides a reading or measurement with the calibration reference stand matching an earlier value of the reading or measurement obtained at the factory at the time of manufacture. In some examples, the new calibration value can be computed regardless of whether the acquired measurement was within or outside the expected range, while in other examples, the computation of the new calibration value can be predicated on a finding that the moisture meter was out of calibration.

Following process block 340, the flowchart can proceed via optional connector block 399 to any of several possible extensions of the first method.

Additional aspects or illustrations of the first method and its extensions are described in the Example Uses section above, and elsewhere herein.

Example Method Extensions

Figure 4:
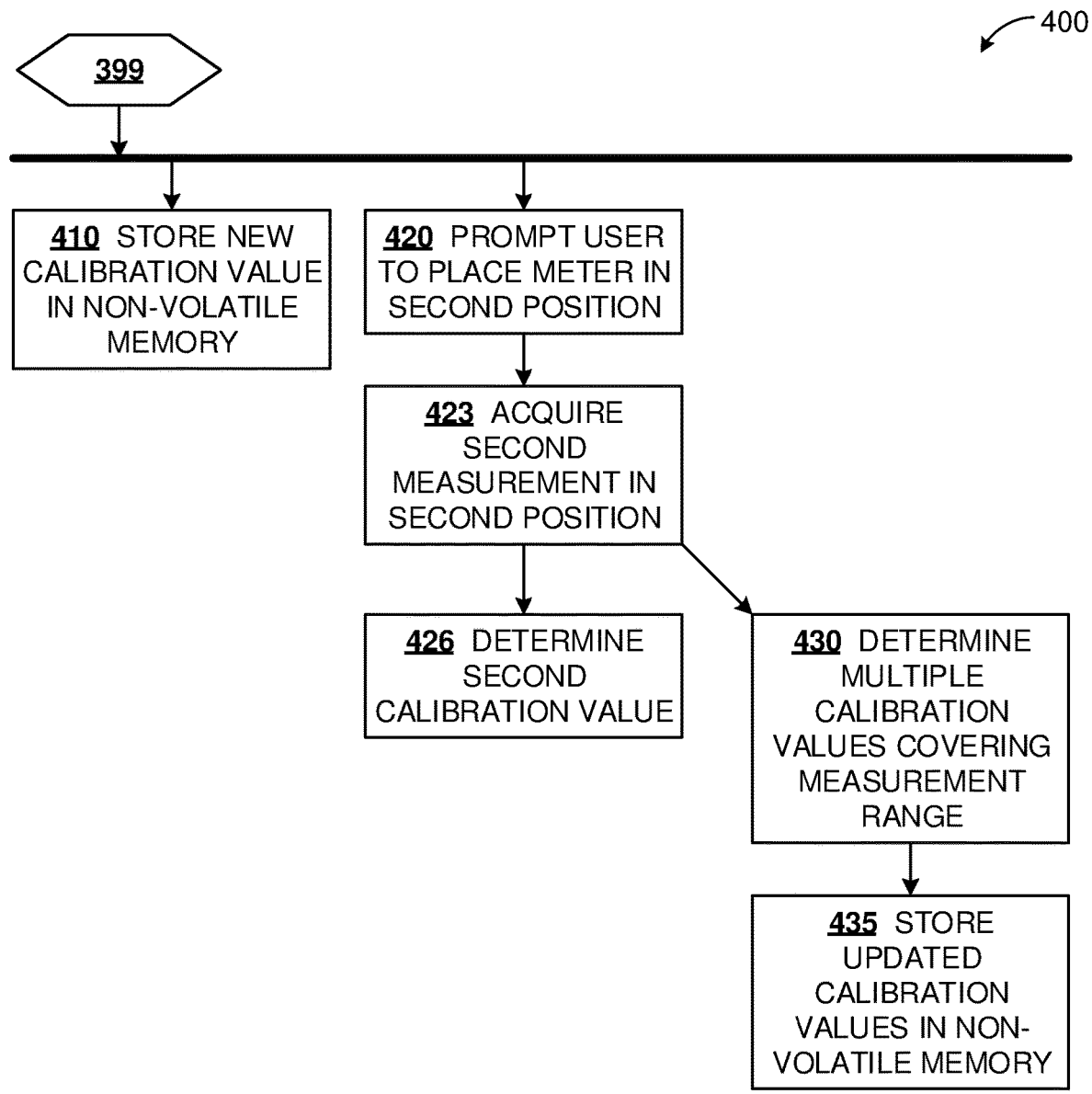
FIG. 4 is a flowchart depicting some example extensions of the first method.

FIG. 4 is a flowchart 400 depicting some example extensions of the first method. Starting with connector block 399, such extensions can follow any of several paths as indicated in FIG. 4.

As a first extension, at process block 410 a new calibration value can be stored in non-volatile memory, to be used in subsequent moisture measurements of samples. The non-volatile memory can be local on board the moisture meter, at another computing device (e.g. smartphone or server) accessible from the moisture meter over a network, or in the cloud. A calibration determination such as an out-of-range finding can likewise be stored locally or remotely. Remote storage of calibration determination can aid with management of a fleet of moisture meters, or can allow access from the factory to track performance of devices in the field.

As another extension, at process block 420, the moisture meter can prompt a user to place the meter in a second position. The second position can be in air, distant (e.g. more than 10 cm) from any moisture bearing sample or other electromagnetic load. At process block 423, a second measurement can be acquired by the moisture meter in the second position. An air measurement can supplement the calibration stand measurement as a second reference point. In examples, the second measurement can be a measurement of capacitance, resistance, or frequency based on an electrical signal passed between the electrodes. Then, at process block 426, a second calibration value can be determined. The second calibration value can be targeted so that the moisture meter provides a reading or measurement with the air environment matching an earlier value of the reading or measurement obtained at the factory at the time of manufacture.

In some examples, the calibration of the moisture meter can be specified by two points, one obtained with the calibration reference, and another in the second position (e.g. air). The two point calibration can be represented in the form of a straight line, for example as coefficients of an equation representing the straight line, or as representative points on the straight line, with suitable scaling or encoding.

In some embodiments, the calibration can be stored as a look-up table, for example with entries for every 1% of moisture content. Thus, the two point calibration can be augmented to obtain additional calibration points. This is illustrated by a third extension to the method of FIG. 3, which branches to process block 430 after block 420, 423. At process block 430, multiple calibration values can be determined covering the measurement range of the moisture meter, e.g. by interpolation between the new and second calibration values, or by extrapolation beyond the new or second calibration values. At process block 435, updated calibration values can be stored locally or remotely in non-volatile memory.

In other examples, a single reference point can suffice for calibration of the moisture meter, i.e. just the calibration value obtained from the measurement with the calibration reference stand. For such examples, the calibration shift at zero moisture can be less significant than the calibration shift at the middle or upper end of the measurement range of the moisture meter. Accordingly, a one point calibration can be represented in the form of a straight line passing through the origin, i.e. a point where actual and measured moisture are both zero, or through another fixed point. In an illustration discussed above, measured moisture m=1.9%, actual moisture M=0% can be such a fixed point. The fixed point can be determined at the factory. The one point calibration can be represented in various ways, for example, as a slope of the straight line, as a calculated value at the equivalent moisture content of the calibration reference stand, or as an interpolated lookup table.

In further examples, calibration of the moisture meter can incorporate deviations from linearity, which can be due to nonlinearities of electronic components or saturation effects of electromagnetic loads in a capacitive moisture sensing circuit. For such examples, a series of more than two calibration points can be required. In some examples, such additional measurements can be made at block 430 to measure additional points to obtain additional calibration values over the measurement range of the moisture meter. In some examples, the updated calibration values can be stored in the form of a table, one calibration value for each respective point at which calibration measurements were made. In other examples, the updated calibration values can be stored for a series of points different from the points at which measurements were made. The updated calibration values can be derived from the measured points by interpolation. To illustrate, measurements can be made for 0%, 10%, 20% and 30% true moisture content, and can be interpolated in 1% steps. Interpolation can also be used to invert the calibration values so that the stored calibration values can be accessed based on uncalibrated moisture measurements. To illustrate, measurements at 20% and 30% can be used to determine that an uncalibrated measurement of 30% corresponds to a calibrated reading of 28%, which can be found by interpolation and stored in a table entry for 30% uncalibrated. In additional examples, the calibration values can be stored as coefficients of a functional form, for example C0 indicating an offset at zero moisture (true or uncalibrated), C1 indicating a slope between zero and the equivalent moisture level of the calibration reference stand, and C2 indicating a quadratic correction. In such a representation, calibrated moisture content CMC can be expressed as a function of uncalibrated moisture content UMC by an equation $CMC=C0+C1 \cdot UMC+C2 \cdot UMC^2$, or an equivalent functional form.

In still further examples, additional measurements at block 430 can be used with a linear calibration formula, by averaging or performing a least squares fit to reduce effects of measurement error in one or two measurements.

Second Example Method

Figures 5, 6:
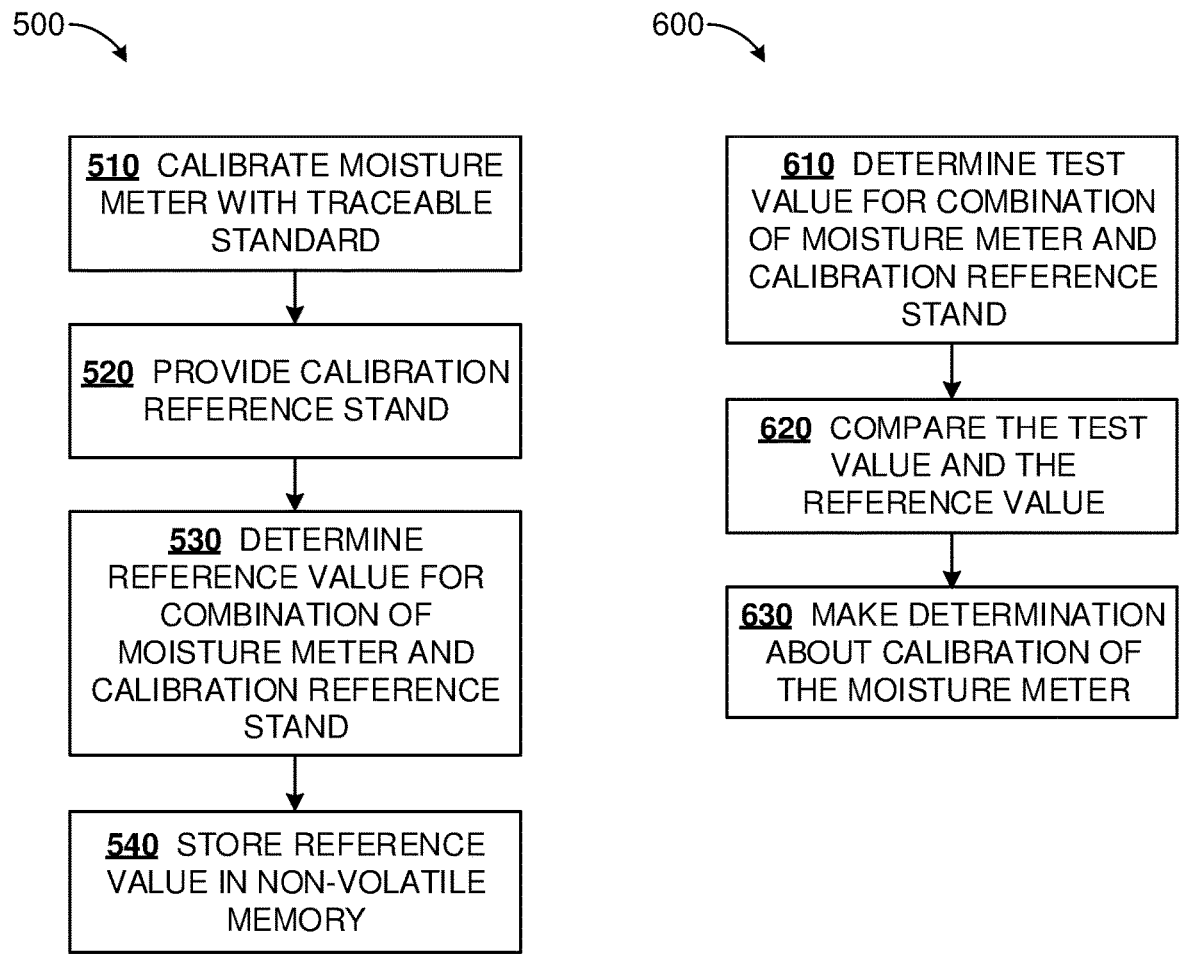
FIG. 5 is a flowchart of a second example method according to the disclosed technologies.
FIG. 6 is a flowchart of a third example method according to the disclosed technologies.

FIG. 5 is a flowchart 500 of a second example method according to the disclosed technologies. This method describes provisioning a moisture meter with an associated calibration reference stand, and can be performed at a factory by a manufacturer.

At process block 510, a moisture meter can be calibrated with a traceable standard, such as a NIST-traceable standard, or another authoritative standard. At process block 520, a calibration reference stand can be provided. In examples, the calibration reference standards can by manufactured in parallel with the manufacture of the moisture meters. Then, at process block 530, a reference value can be determined for the combination of the moisture meter and the calibration reference stand. The reference value can be a measurement, a moisture reading, or a calibration coefficient. At process block 540, the reference value can be stored in local non-volatile memory, or in remote non-volatile memory coupled to the moisture meter over a network.

The reference value can be specific to a combination of a particular moisture meter and a particular calibration reference stand. With the reference value, the moisture meter and the calibration reference stand can be individually matched to each other. In some examples, a calibration stand can be unique to a single moisture meter. In other examples, a given calibration stand can be matched to multiple moisture meters, with a respective reference value for each moisture meter.

Additional aspects or illustrations of the second method are described in the Example Uses section above, and elsewhere herein.

Third Example Method

FIG. 6 is a flowchart 600 of a third example method according to the disclosed technologies. This method uses a test value and a reference value for a combination of a moisture meter and an associated calibration reference stand to make a determination about the calibration of the moisture meter.

At process block 610, a test value can be determined for the combination of the moisture meter and its associated calibration reference stand. In examples, process block 610 can be performed by suitably positioning the moisture meter on the calibration reference stand, and taking a moisture reading or a special test measurement which can be the test value. Alternatively, the test value can be derived from the measurement or reading. At process block 620, the test value can be compared with a reference value for the same combination of the moisture meter and calibration reference stand. Commonly, the test value T and the reference value R can be like quantities, so that comparison can be simply a matter of comparing the numerical magnitudes of the test and reference values, e.g. as |T−R|. At process block 630 and based on the comparison, a determination about calibration of the moisture meter can be made. For example, if |T−R| exceeds a threshold, then the moisture meter can be determined to be out of calibration. Alternatively or additionally, the determination can include a new calibration value, for example $C_{NEW}=C_{OLD} \cdot (R/T)$, where $C_{NEW}$ and $C_{OLD}$ can be the new and old calibration values respectively. To illustrate, if the old calibration value $C_{OLD}$ provided a moisture reading of T when multiplied by a measurement value q, i.e. $T=q \cdot C_{OLD}$, then with the new calibration value $C_{NEW}$, a moisture reading of $q \cdot C_{NEW}=q \cdot C_{OLD} \cdot (R/T)=T \cdot (R/T)=R$, as desired.

Additional aspects or illustrations of the third method are described in the Example Uses section above, and elsewhere herein.

Example Coupling Between Electromagnetic Load and Moisture Sensor

FIGS. 7A-7E are diagrams illustrating field patterns for several example configurations of a moisture meter with or without a coupled electromagnetic load. Each of FIGS. 7A-7D is an elevation having similar orientation as FIG. 2B, or as section 147 of FIG. 1, while FIG. 7E is shown in top view, i.e. similar orientation as FIG. 2A.

FIG. 7A is a diagram 720 of a baseline configuration of a moisture meter 710 without any electromagnetic load. For example, the moisture meter 710 can be suspended in air 722. Moisture meter 710 can include a moisture sensor represented by a pair of electrodes 715, 716. Commonly, electrodes 715, 716 can be excited by an AC or RF oscillatory signal. FIG. 7A illustrates, in simplified form, a field pattern comprising a bundle 705 of arced electric field lines going from electrode 715 to electrode 716. This field pattern can correspond to an instantaneous snapshot with electrode 715 having a positive charge while electrode 716 has a negative charge. The field pattern extends some distance from the electrodes 715, 716, which can provide moisture sensor 710 with depth sensitivity. The density of field lines can be proportional to the local strength (amplitude) of the electric field.

FIG. 7B is a diagram 730 of an operational configuration of a moisture meter 710 placed on a homogeneous sample medium 732, such as wood or concrete. The presence of a dielectric, including but not limited to moisture, can impact the field distribution in the vicinity of electrodes 715, 716. For example, electric fields in the sample medium 732 can induce polarization of the medium, which can reduce the electric field in the medium as illustrated by the fewer field lines in FIG. 7B compared to FIG. 7A. The volumetric energy density of an electric field can be described as proportional to $|E|^2$, where E is the local amplitude of electric field. Thus, with charge on electrodes 715, 716 held constant, the presence of a dielectric 732 in the field region also decreases the stored electrical energy. These effects can be described in circuit terms as increasing the capacitance between electrodes 715, 716. (A capacitance C storing a charge Q has a stored energy proportional to $Q^2/C$.)

Because the presence of moisture or another dielectric material can impact the field pattern and affect the operation of a circuit providing excitation to the electrodes 715, 716, the material 732 can be said to be an electromagnetic load. Electromagnetic loads are not limited to moisture or dielectric materials, but can also be implemented by conductors such as a metal sheet. Further, an electromagnetic load can be provided in a form having long term stability, suitable for a calibration reference stand. The remaining FIGS. 7C-7E illustrate some configurations of an electromagnetic load in example configurations which can be used with a calibration reference stand.

FIG. 7C is a diagram 740 of a moisture meter 710 placed in a calibration reference stand having a metal sheet electromagnetic load 743. Metal load 743 supports substantially zero electric field within the metal, thus greatly reducing the volume in which electric field energy is stored. As described in context of FIG. 7B, the stored energy is reduced and the capacitance is increased, similar to the configuration of FIG. 7B. In this way, the metal sheet load 743 can emulate a moisture bearing sample 732. The equivalent moisture content for metal load 743 can depend on the size of the metal load 743, the spacing between the metal load 743 and the electrodes 715, 716, as well as other details of the electrode geometry of electrodes 715, 716 and characteristics (such as dielectric constant) of any platform material interposed between the metal load 743 and electrodes 715, 716.

FIGS. 7B-7C illustrate loads 732, 743 that are directly beneath the electrodes 715, 716. However, this not a requirement. FIGS. 7D-7E illustrate loads that are centrally located between electrodes 715, 716 and offset to the side of electrodes 715, 716, respectively.

FIG. 7D is a diagram 750 showing an electromagnetic load 753 symmetrically disposed beneath moisture sensor 710. Load 753 can be made of metal or a high-dielectric constant material. A comparison of FIGS. 7A, 7D shows that in the space not occupied by the load 753, the electric field can remain substantially unchanged, while within the volume of load 753, the electric field can be attenuated, even to nearly zero if the load 753 is metal or of a particularly high dielectric constant. Thus, even though the field outside the volume of load 753 can remain unchanged, the volume of stored energy is decreased by about the volume of load 753, which can provide an increase in capacitance that emulates a moisture-bearing sample.

FIG. 7E is a plan view 760 showing an electromagnetic load 763 offset to one side of electrodes 765, 766. Load 763, which can be dielectric or metal, draws fringing fields of the electrodes 765, 766 towards the load 763, while maintaining very little if any electric field within the volume of 763. Once again, the effect is to reduce the stored electrical energy and increase the capacitance between electrodes 765, 766, as compared to the configuration of FIG. 7A. Thus, an offset load 763 can also be deployed in a calibration reference stand.

Many other configurations of electromagnetic loads and field patterns can be employed within the scope of disclosed technologies.

Example Hardware Architecture

Figure 8:
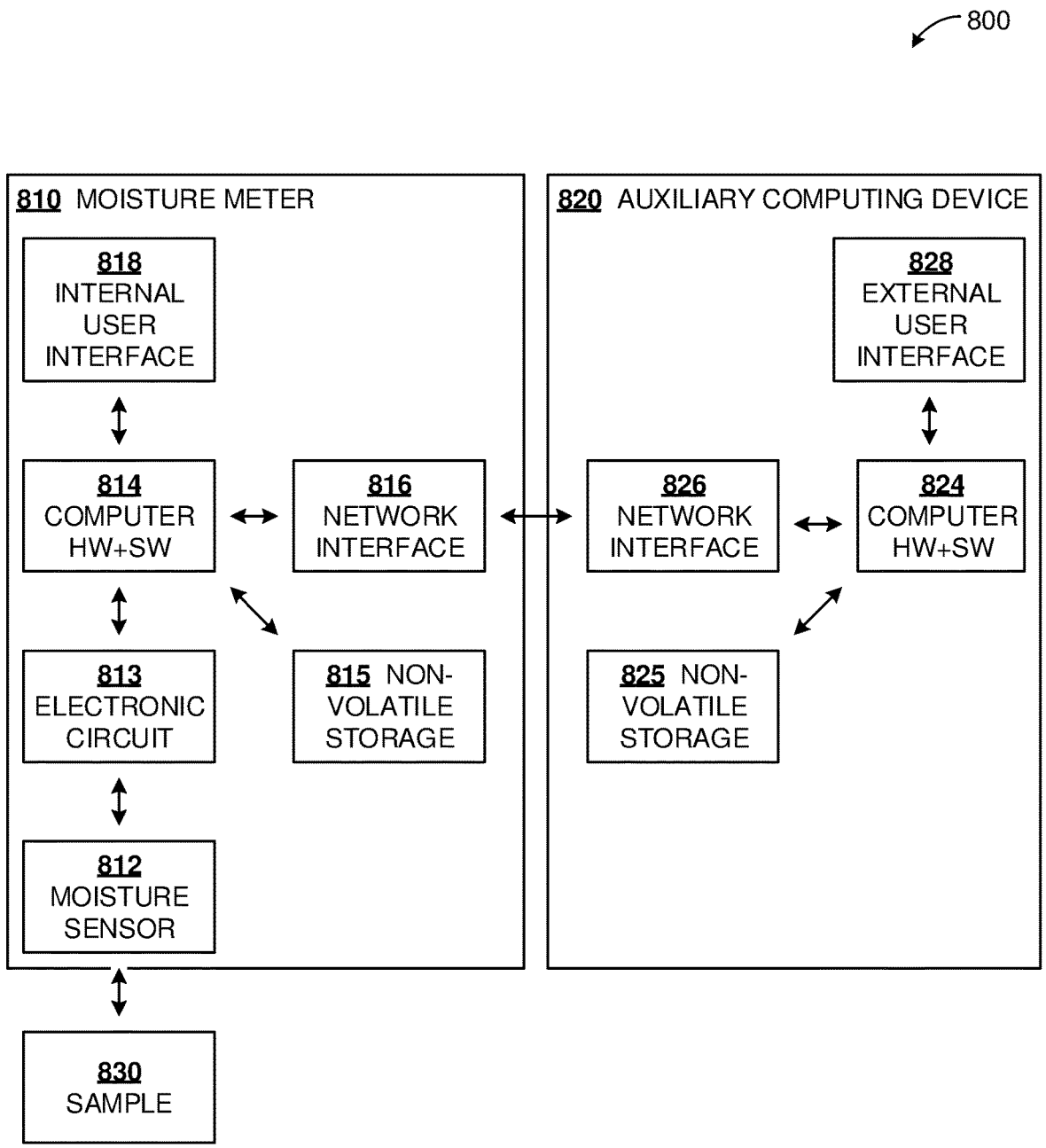
FIG. 8 is a block diagram of an example hardware architecture for implementing disclosed technologies.

FIG. 8 is a block diagram 800 of an example hardware architecture for implementing disclosed technologies. Moisture meter 810 can be similar to that illustrated in FIG. 1, and can incorporate a computer 814 coupled to a moisture sensor 812 through electronic circuits 813, and an integrated user interface 818. Electronics 813 can provide a stimulus signal at the sensor 812 and can detect the response with a sample 830 proximate to the electrodes of sensor 812. The user interface 818 can include a keypad similar to 120 and a display similar to 125. The computer 814 can be based on a microprocessor or microcontroller with associated peripherals as described herein or as known in the computer art. For example, digital input/output ports or a peripheral bus can be used to interface with the user interface 818, with the electronics 813, or indirectly with the moisture sensor 812.

In some examples, the moisture meter 810 can include a network interface 816 (such as Bluetooth, Wi-Fi, infrared link, another personal area network, or a proprietary wireless connection) over which the moisture meter 810 can be coupled, directly or indirectly, to an auxiliary computing device 820 having its own network interface 826 and processor 824. Auxiliary computing device 820 can be a smartphone, tablet, portable or fixed computer, television set, or remote control device. In varying examples, the technologies described herein can be implemented wholly on moisture meter 810, or distributed between the moisture meter 810 and auxiliary computing device 820. Particularly, auxiliary computing device 820 can include its own user interface 828 on which readings, alerts, or notifications described herein can be displayed, or from which user input can be provided to control the operations of moisture meter 810. In some examples, internal user interface 818 can be omitted from the moisture meter 810.

Computer 814, incorporating one or more hardware processors, can operate the moisture sensor 812 through electronics 813, can communicate with external or internal user interface 818, 828, and/or can execute instructions to perform any of the processes, methods, or variations thereof as described herein. Either moisture meter 810 or auxiliary computer 820 can incorporate non-volatile storage 815, 825 for storing calibration values or software of the disclosed technologies, as described herein.

The disclosed technologies can also be embodied in a system including a calibration reference stand, such as stand 200, and a moisture meter 810. The meter 810 can incorporate a computer 814 and associated computer-readable media 815 storing calibration values as well as instructions which can be executed to perform the disclosed methods. In alternative embodiments, external computer-readable media 825 can be part of the system and can be used to store executable instructions or calibration data.

A Generalized Computer Environment

Figure 9:
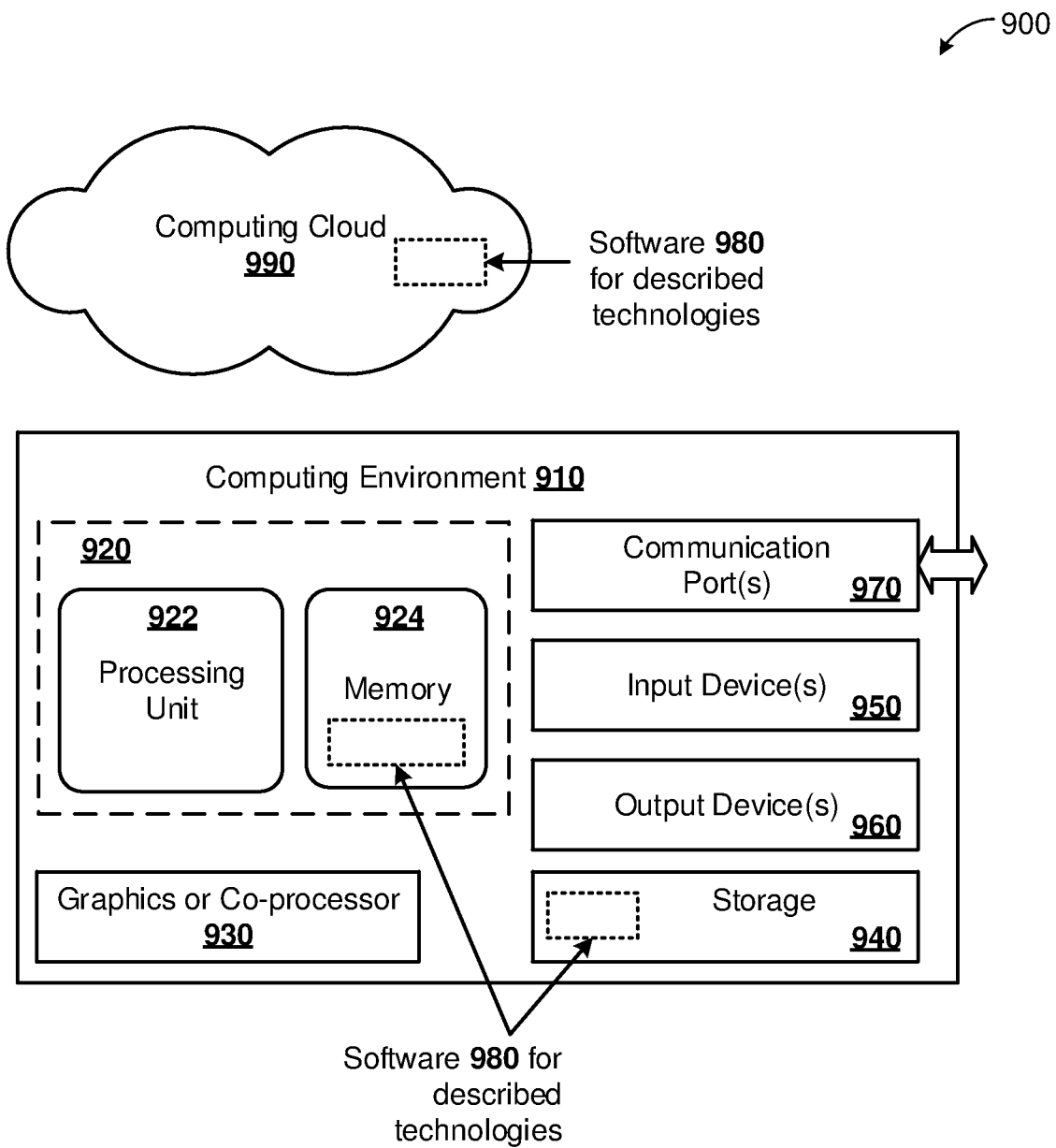
FIG. 9 is a diagram schematically depicting a computing environment suitable for implementation of disclosed technologies.

FIG. 9 illustrates a generalized example of a suitable computing system 900 in which described examples, techniques, and technologies can be implemented, including configuration, deployment, or operation, of calibration determinations for a moisture meter. The computing system 900 is not intended to suggest any limitation as to scope of use or functionality of the present disclosure, as the innovations can be implemented in diverse general-purpose or special-purpose computing systems.

With reference to FIG. 9, computing environment 910 includes one or more processing units 922 and memory 924. In FIG. 9, this basic configuration 920 is included within a dashed line. Processing unit 922 executes computer-executable instructions, such as for implementing components of a software architecture for configuring or testing a moisture meter with its calibration reference stand, any of the methods described herein, or various other architectures, components, data structures, handlers, managers, or modules described herein. Processing unit 922 can be a general-purpose central processing unit (CPU), a processor in an application-specific integrated circuit (ASIC), or any other type of processor. In a multi-processing system, multiple processing units execute computer-executable instructions to increase processing power. Computing environment 910 can also include a graphics processing unit or co-processing unit 930. Tangible memory 924 can be volatile memory (e.g., registers, cache, or RAM), non-volatile memory (e.g., ROM, EEPROM, or flash memory), or some combination thereof, accessible by processing units 922, 930. The memory 924 stores software 980 implementing one or more innovations described herein, in the form of computer-executable instructions suitable for execution by the processing unit(s) 922, 930.

A computing system 910 can have additional features, such as one or more of storage 940 (representing e.g. storage for executable instructions, calibration data, configuration data, or state information of a moisture meter), input devices 950, output devices 960, or communication ports 970. An interconnection mechanism (not shown) such as a bus, controller, or network interconnects the components of the computing environment 910. In some examples, operating system software (not shown) provides an operating environment for other software executing in the computing environment 910, and coordinates activities of the components of the computing environment 910.

The memory 924 or storage 940 can also store acquired or calculated data, including measurements, readings, or statistics of a moisture meter. The memory 924 or storage 940 can also store some or all of a configuration file, an auxiliary input file, and/or other configuration and operational data. The tangible storage 940 can be removable or non-removable, and includes flash memory, magnetic disks, magnetic tapes or cassettes, CD-ROMs, DVDs, or any other medium which can be used to store information in a non-transitory way and which can be accessed within the computing environment 910. The storage 940 stores instructions of the software 980 (including instructions and/or data) implementing one or more innovations described herein.

The input device(s) 950 can be a mechanical, touch-sensing, or proximity-sensing input device such as a push-button, keypad, keyboard, mouse, pen, touchscreen, or trackball, a voice input device, a scanning device, or another device that provides input to the computing environment 910. The output device(s) 960 can be a display, indicator lamp, printer, speaker, optical disk writer, or another device that provides output from the computing environment 910.

The communication port(s) 970 enable communication over a communication medium to another computing entity. The communication medium conveys information such as computer-executable instructions, audio or video input or output, calibration data, readings, alerts, notifications, or other data in a modulated data signal. A modulated data signal is a signal that has one or more of its characteristics set or changed in such a manner as to encode information in the signal. By way of example, and not limitation, communication media can use an electrical, optical, RF, acoustic, or other carrier.

In some examples, computer system 900 can also include a computing cloud 990 in which instructions implementing all or a portion of the disclosed technology can be executed. Any combination of memory 924, storage 940, and computing cloud 990 can be used to store software instructions and data of the disclosed technologies. A local or datacenter computing environment 910 can utilize the computing cloud 990 to obtain computing services and perform computing operations (e.g., data processing, data storage, and the like).

In some examples, software embodiments of the disclosed technologies can be deployed on a smartphone, tablet, portable or fixed computer, television set, memory card, memory stick, or a handheld remote control device.

The present innovations can be described in the general context of computer-executable instructions, such as those included in program modules, being executed in a computing system on a target real or virtual processor. Generally, program modules or components include routines, programs, libraries, objects, classes, components, data structures, etc. that perform particular tasks or implement particular data types. The functionality of the program modules can be combined or split between program modules as desired in various embodiments. Computer-executable instructions for program modules can be executed within a local or distributed computing system.

The terms "system", "environment", and "device" are used interchangeably herein. Unless the context clearly indicates otherwise, neither term implies any limitation on a type of computing system, computing environment, or computing device. In general, a computing system, computing environment, or computing device can be local or distributed, and can include any combination of special-purpose hardware and/or general-purpose hardware and/or virtualized hardware, together with software implementing the functionality described herein. Virtual processors, virtual hardware, and virtualized devices are ultimately embodied in one or another form of physical computer hardware.

General Considerations

As used in this disclosure, the singular forms "a", "an", and "the" include the plural forms unless the context clearly dictates otherwise. Additionally, the terms "includes" and "incorporates" mean "comprises". Further, the term "coupled" encompasses mechanical, electrical, magnetic, optical, wireless, as well as other practical ways of coupling or linking items together, and does not exclude the presence of intermediate elements between the coupled items. Furthermore, as used herein, the terms "or" or "and/or" mean any one item or combination of items in the phrase.

The systems, methods, and apparatus described herein should not be construed as being limiting in any way. Instead, this disclosure is directed toward all novel and non-obvious features and aspects of the various disclosed embodiments, alone and in various combinations and subcombinations with one another. The disclosed systems, methods, and apparatus are not limited to any specific aspect or feature or combinations thereof, nor do the disclosed things and methods require that any one or more specific advantages be present or problems be solved. Furthermore, any features or aspects of the disclosed embodiments can be used in various combinations and subcombinations with one another.

Although the operations of some of the disclosed methods are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed things and methods can be used in conjunction with other things and methods. Additionally, the description sometimes uses terms like "access", "acquire", "analyze", "apply", "average", "calculate", "calibrate", "check", "compare", "compute", "determine", "digitize", "display", "encode", "enter", "evaluate", "execute", "filter", "generate", "input", "incorporate", "measure", "make", "obtain", "output", "process", "provide", "receive", "repeat", "round", "retrieve", "scale", "select", "sense", "store", "transform", "transmit", and "use" to denote actual operations that are performed by or managed by a computer. The actual operations that correspond to these terms will vary depending on the particular implementation and are readily discernible by one of ordinary skill in the art.

Theories of operation, scientific principles, or other theoretical descriptions presented herein in reference to the apparatus or methods of this disclosure have been provided for the purposes of better understanding and are not intended to be limiting in scope. The apparatus and methods in the appended claims are not limited to those apparatus and methods that function in the manner described by such theories of operation.

Any of the disclosed methods can be implemented as computer-executable instructions or a computer program product stored on one or more computer-readable storage media, such as tangible, non-transitory computer-readable storage media, and executed on a computing device (e.g., any available computing device, including tablets, smartphones, or other mobile devices that include computing hardware). Tangible computer-readable storage media are any available tangible media that can be accessed within a computing environment (e.g., one or more optical media discs such as DVD or CD, volatile memory components (such as DRAM or SRAM), or nonvolatile memory components (such as flash memory or hard drives)). By way of example, and with reference to FIG. 9, computer-readable storage media include memory 924, and storage 940. The terms computer-readable storage media or non-volatile memory do not include signals and carrier waves. In addition, the terms computer-readable storage media or non-volatile memory do not include communication ports (e.g., 970) or communication media.

Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network, a cloud computing network, or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in Adobe Flash, assembly language, B #, C, C++, C #, Curl, Dart, Fortran, Haskell, Java, JavaScript, Julia, Lisp, Matlab, Octave, Perl, Python, R, Ruby, Rust, SAS, SPSS, SQL, WebAssembly, any derivatives thereof, or any other suitable programming language, or, in some examples, markup languages such as HTML or XML, using CSS, JSON, or any combination of suitable languages, libraries, packages, or scripts. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, infrared, and optical communications), electronic communications, or other such communication means.

The disclosed methods, apparatus, and systems should not be construed as limiting in any way. Instead, the present disclosure is directed toward all novel and nonobvious features and aspects of the various disclosed embodiments, alone and in various combinations and subcombinations with one another. The disclosed methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope of these claims.

I claim:

1. A computer-implemented method comprising:

receiving an input at a moisture meter to trigger a determination of a new calibration value of the moisture meter;

obtaining a first measurement of a calibration reference stand with the moisture meter;

analyzing the first measurement with reference to a predetermined calibration value of the calibration reference stand and based on the moisture meter being positioned on a sensor pad of the calibration reference stand;

making the determination of the new calibration value based on the analyzing;

responsive to the moisture meter being positioned in a second position spatially apart from any electromagnetic load, obtaining a second measurement with the moisture meter; and determining a second calibration value of the moisture meter.

2. The computer-implemented method of claim 1, further comprising:

based on the new and second calibration values, determining a plurality of updated calibration values covering a measurement range of the moisture meter; and storing the plurality of updated calibration values in non-volatile memory of the moisture meter.

3. The computer-implemented method of claim 1, further comprising prompting a user to position the moisture meter in the second position.

4. A calibration reference stand, comprising:

a platform;

a sensor pad and a electromagnetic load supported by the platform;

wherein the sensor pad defines a location at which a sensor of a moisture meter can be received, and the electromagnetic load is positioned spatially apart from the location; and wherein the calibration reference stand is configured to present the electromagnetic load to the sensor as equivalent to a predetermined moisture content value, when the sensor is positioned at the location.

5. The calibration reference stand of claim 4, further comprising a plurality of legs extending downwardly from the platform.

6. The calibration reference stand of claim 4, wherein the electromagnetic load is a metal sheet.

7. The calibration reference stand of claim 4, wherein the electromagnetic load extends spatially beyond the sensor in at least one direction when the sensor is positioned at the location.

8. The calibration reference stand of claim 4, wherein the platform comprises an insulator, at least part of which is situated between the electromagnetic load and the location.

9. The calibration reference stand of claim 4, wherein the calibration reference stand and the moisture meter are individually matched to each other.

10. The calibration reference stand of claim 4, wherein the location is defined by one or more structural features of the sensor pad that facilitate reproducible positioning of the sensor at the location.

11. The calibration reference stand of claim 10, wherein the one or more structural features comprise a rectangular relief at a surface of the sensor pad.

* * * * *